United States Patent [19]

Murakami et al.

[11] Patent Number: 5,155,043
[45] Date of Patent: Oct. 13, 1992

[54] METHOD FOR PREPARING OPTICALLY ACTIVE SUBSTANCES

[75] Inventors: Nobuo Murakami; Masami Mochizuki, both of Sodegaura, Japan

[73] Assignee: Idemitsu Kosan Company Limited, Tokyo, Japan

[21] Appl. No.: 438,265

[22] Filed: Mar. 23, 1990

[30] Foreign Application Priority Data

Apr. 6, 1989 [JP] Japan .................................. 1-85813

[51] Int. Cl.$^5$ .............................................. C12P 41/00
[52] U.S. Cl. ..................................... 435/280; 435/146; 435/145; 435/142
[58] Field of Search ................. 435/280, 145, 146, 142

[56] References Cited

U.S. PATENT DOCUMENTS 4,204,044  5/1980  Suhara et al. .................... 435/876 X

FOREIGN PATENT DOCUMENTS

| 0000560 | 2/1979 | European Pat. Off. . |
| 0224246 | 6/1987 | European Pat. Off. . |
| 0356912 | 3/1990 | European Pat. Off. . |
| 0357787 | 3/1990 | European Pat. Off. . |
| 173788 | 1/1985 | Japan .................... 435/146 |
| 225499 | 9/1989 | Japan .................... 435/280 |

Primary Examiner—Carolyn Elmore
Attorney, Agent, or Firm—Frishauf, Holtz, Goodman & Woodward

[57] ABSTRACT

Optically active substances are prepared by the asymmetric hydrolysis of

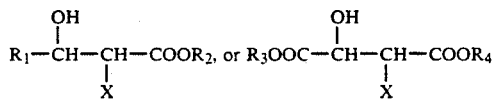

with specific microorganisms.

18 Claims, No Drawings

METHOD FOR PREPARING OPTICALLY ACTIVE SUBSTANCES

BACKGROUND OF THE INVENTION

The present invention relates to a method for preparing optically active substances and, more particularly, to a method for preparing halohydrin-containing esters or arboxylic acids with high optical purity by efficient symmetric hydrolysis of halohydrin-containing esters with specific microbes.

Optically active halohydrins are useful as starting materials for ferroelectric liquid crystals, pharmaceuticals and pesticides, and techniques for preparing halohydrins having optically high purity with improved efficiency are in demand. However, never until now is there any report on methods for making optically active monocarboxylic acid containing halohydrins or their esters with microbes. Heretofore, it has been reported to produce L-threochloromalic acid from chlorofumaric acid with fumarase as one method for producing optically active dicarboxylic acids containing halohydrins or their esters. However, this method is disadvantageous in that the starting materials are not only expensive but also substantially difficult to obtain. Besides, some reports are found in Mem. Fac. Sci. Kyushu Univ., Ser. C., 11(2), 217-224 (1974); Tetrahedron 36(1), 87-90 (1980); and J. Am. Chem. Soc. 110, 7538-7539 (1988), but they all have a disadvantage of using expensive starting materials and other defects.

The present inventors have thus made intensive and extensive studies of the preparation of optically active substances containing halohydrins and, in consequence, have found that they can efficiently be prepared by the asymmetric hydrolysis of halohydrin-containing esters with a specific microbe.

SUMMARY OF THE INVENTION

More specifically, the present invention provides a method for preparing an optically active substance expressed by the following general formula:

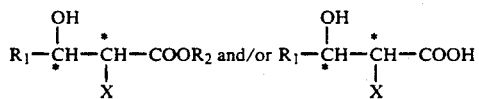

wherein $R_1$ stands for a hydrogen atom, an alkyl group or a substituted or unsubstituted phenyl group, $R_2$ denotes an alkyl group and X indicates a halogen atom, said method being characterized by the asymmetric hydrolysis of an ester expressed by the following formula:

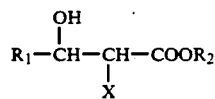

wherein $R_1$, $R_2$ and X have the same meaning as defined above, with a microorganism capable of asymmetrically hydrolyzing said ester and a method for preparing optically active substances expressed by the following general formulae:

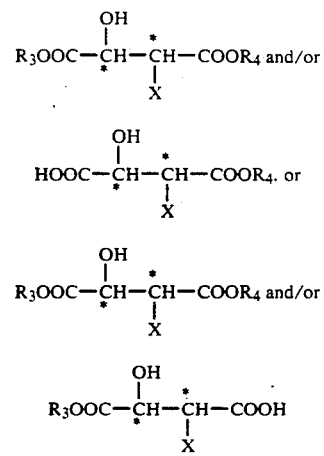

wherein $R_3$ and $R_4$, which may be identical with or different from each other, each stand for an alkyl group and X denotes a halogen atom, said method being characterized by the asymmetric hydrolysis of an ester expressed by the following general formula:

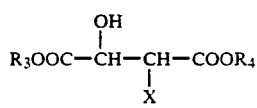

wherein $R_3$, $R_4$ and X have the same meanings as defined above, with a microorganism capable of asymmetrically hydrolyzing said ester.

DETAILED DESCRIPTION OF THE INVENTION

As the starting materials in the present invention, use may be made of a halohydrin-containing monocarboxylate expressed by the general formula I:

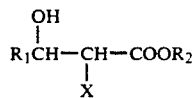

wherein $R_1$, $R_2$ and X have the same meanings as defined above, or a halohydrin-containing dicarboxylate expressed by the general formula II:

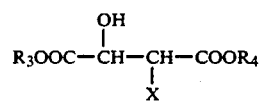

wherein $R_3$, $R_4$ and X have the same meanings as defined above. The halohydrin-containing esters having the general formulae I and II may be of either erythro- or threo-forms. More illustratively, X in the general formulae I and II stands for Cl, Br and I. When $R_1$ stands for an alkyl group, it may be a lower alkyl group having 1 to 6 carbon atoms or a higher alkyl group having at least 7 carbon atoms. More illustratively, it denotes a methyl, ethyl, propyl, heptyl, octyl group, etc. The substituted phenyl group may be a phenyl group, one or more of hydrogen atoms of which are substituted by a halogen atom, a hydroxyl group, a methoxy group or an alkyl (e.g., methyl, ethyl or propyl) group. $R_2$, $R_3$ and $R_4$ may be identical with or different from each other, and each stand for a lower alkyl group having 1 to 6 carbon atoms or a higher alkyl group having at least 7 carbon atoms. More illustratively, they indicate methyl, ethyl, propyl, heptyl, and octyl groups.

In the present invention, any microorganisms suitable for the asymmetric hydrolysis of the above halohydrin-containing esters may be used, inclusive of those belonging to the following genera: Achromobacter, Acinetobacter, Arthrobacter, Ervinia, Enterobacter, Klebsiella, Chromobacterium, Corynebacterium, Pseudomonas, Bacteridium, Bacillus, Paracoccus, Flavobacterium, Brevibacterium, Proteus, Micrococcus, Rhodococcus, Candida, Nocardia, and Rhodotorula. Illustrative reference is made to *Achromobacter lyticus* IFO 12725, *Achromobacter lyticus* IFO 12726, *Acinetobacter calcoaceticus* IFO 12552, *Arthrobacter* sp. ATCC 27778, *Erwinia herbicola* ATCC 21434, *Enterobacter* sp. IAM 12247, *Klebsiella pneumoniae* IFO 3318, *Chromobacterium chocolatum* IFO 3758, *Corynebacterium flavescens* IAM 1642, *Corynebacterium hydrocarbooxydans* ATCC 21767, *Pseudomonas aeruginosa* ATCC 15522, *Pseudomonas aeruqinosa* ATCC 15523, *Pseudomonas diminuta* IFO 13181, *Pseudomonas dimimuta* IFO 13182, *Pseudomonas pseudoalcaligenes* ATCC 12815, *Pseudomonas oleovorans* ATCC 29347, *Bacteridium* sp. CBS 495-74, *Bacteridium* sp. CBS 496-74, *Bacillus cereus* IFO 3131, *Bacillus subtilis* IFO 3108, *Bacillus* sp. CBS 494-74, *Paracoccus denitrificans* IFO 13301, *Flavobacterium lutescens* IFO 3084, *Brevibacterium* sp. CBS 717-73, *Brevibacterium imperiale* CBS 498-74, *Brevibacterium paraffinoliticum* ATCC 21195, *Proteus mirabilis* IFO 3849, *Micrococcus* sp. CBS 497-74, *Micrococcus paraffinolyticus* ATCC 15582, *Rhodococcus erythropolis* IFO 12320, *Rhodococcus equi* IFO 3730, *Candida rugosa* ATCC 14830 and *Rhodotorula minuta* var. texensis IFO 879, *Norcardia* sp. ATCC 21145. These microorganisms may be used alone or in combination of two or more.

The microorganisms may be applied in varied forms. For instance, proliferating, resting and immobilized microorganisms may be used. Further, use may be made of microbial extracts or culture solution. Microbial immobilization may be achieved by conventional immobilization techniques such as carrier bonding method, crosslinking method, inclusion method and the like. For extraction methods, microbial cells in a suspension are subjected to crushing by using ultrasonics waves, a French press, a high-pressure homogenizer, etc. and then by solid-liquid separation by, for example, centrifugation to give the soluble fraction.

No particular limitation is placed on culture media for culturing the above microorganisms. Use may thus be made of any medium suitable for the growth of the above microorganisms, e.g., a bouillon medium.

The starting halohydrin-containing esters expressed by the above general formulae I and II may be subjected to asymmetric hydrolysis at a concentration of 1 to 500 g/l, preferably 5 to 100 g/l at a temperature of 0° to 60° C., preferably 10° to 40° C. and in a pH range of 4 to 11, preferably 6 to 8. The reaction may be carried out under aerobic or anaerobic conditions, which may be determined while taking the nature of the microorganisms used into consideration. It is understood that such reaction conditions may be selected depending upon the microorganisms used with a view to keeping them stable and obtaining the desired product with efficiency.

The starting halohydrin-containing esters expressed by the above general formula I or II may be added to a reaction system at a start of the reaction or added to the system from the outset with its additional feeding at any suitable time after the initiation of the reaction. The feed may be added to the reaction system in a batch or batches, or in continuous manners.

Thus, the halohydrin-containing monocarboxylates expressed by the above general formula I yield the halohydrin-containing, optically active esters and/or carboxylic acids expressed by the formulae:

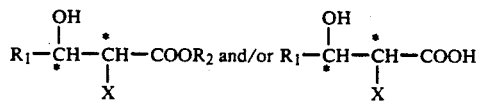

wherein $R_1$, $R_2$ and X have the same meanings as already indicated. The dicarboxylates expressed by the general formula II also yield the halohydrin-containing, optically active esters and/or monocarboxylic monoesters expressed by the formulae:

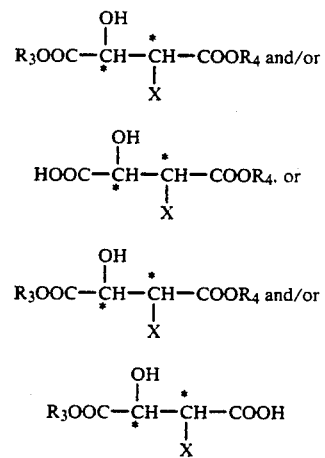

wherein $R_3$, $R_4$ and X have the same meanings as already indicated. No critical limitation is imposed upon the separation and purification of the resulting products. For instance, reliance may be placed upon conventional means in which distillation is directly applied or before distillation, absorption or desorption with activated charcoal, zeolite, etc. or extraction with organic solvents may be applied.

According to the present invention, the halohydrin-containing esters and carboxylic acids, both having high optical purity, can be produced at low costs and with improved efficiency. The obtained halohydrin-containing, optically active esters and carboxylic acids provide useful intermediates for chemicals, liquid crystals, pharmaceuticals and pesticides.

In the following, the method of the present invention is described in more detail by way of examples.

EXAMPLE 1

*Corynebacterium flavescens* IAM 1642 was inoculated on 150 ml of a bouillon medium (Nissui Seiyaku Co., Ltd.) and cultured at 30° C. overnight. After culturing, the microbial cells were collected and washed, and were then suspended at $OD_{660} = 5$ in a 1/15M phosphate buffer of pH 7 containing 5 g/l of ethyl erythro-2-chloro-3-hydroxybutyrate and a reaction was performed for 7 hours at 30° C. The residues of the substrate added was determined by gas chromatography with a condition of a carrier of PEG-20 M, a column length of 2 meters and a column temperature of 150° C. Consequently, the rate of hydrolysis after the completion of the reaction was found to be 56%. After hydrochloric acid had been added to the reaction solution to regulate its pH to 2, the microbial cells were removed by centrifugation, and the supernatant was then extracted with diethyl ether. After transferring 2-chloro-3-hydroxybutyric acid into the aqueous phase with saturated sodium bicarbonate, ethyl 2-chloro-3-hydroxybutyrate in the ether phase was obtained, followed by drying and evaporation of the solvent in vacuo. On the other hand, 2-chloro-3-hydroxybutyric acid being transferred into the aqueous phase was obtained by regulating its pH to 2 by the addition of hydrochloric acid, extracting with diethyl ether followed by a subsequent drying and evaporation of the solvent in vacuo. It is noted that ethyl 2-chloro-3-hydroxybutyrate and 2-chloro-3-hydroxybutyric acid were identified by gas chromatography. Subsequently, the products were measured in terms of their optical purity by high performance liquid chromatography (Chiralcel OB made by Daicel Chemical Industries, Ltd.) and their rotatory polarization by a polarimeter (SEPA-100 made by Horiba Co., Ltd.). In consequence, it was found that (+)ethyl-erythro-2-chloro-3-hydroxybutyrate with an optical purity of 99% ee and (−)-erythro-2-chloro-3-hydroxybutyric acid with an optical purity of 68% ee were obtained in yields of 0.92 g and 0.85 g, respectively. It is noted that the optical purity of 2-chloro-3-hydroxybutyric acid was determined after converted to the corresponding ethyl ester.

EXAMPLES 2 to 19

The procedure of Example 1 was substantially repeated except that the microorganisms set forth in Table 1 were used in place of *Corynebacterium flavescens* IAM 1642. The results are indicated in Table 1.

TABLE 1

| Example | Microorganisms used | Rate of hydrolysis (%) | Optical purity* (% ee) | Rotatory polarization |
|---|---|---|---|---|
| 2 | *Achromobacter lyticus* IFO12726 | 63 | 31 | + |
| 3 | *Acinetobacter calcoaceticus* IFO12552 | 53 | 69 | − |
| 4 | *Arthrobacter sp.* ATCC27778 | 86 | 99 | − |
| 5 | *Ervinia herbicola* ATCC21434 | 76 | 89 | − |
| 6 | *Enterobacter sp.* IAM12247 | 51 | 17 | − |
| 7 | *Klebsiella pneumoniae* IFO3318 | 83 | 57 | + |
| 8 | *Chromobacterium chocolatum* IFO3758 | 61 | 100 | + |
| 9 | *Pseudomonas oleovorans* ATCC29347 | 22 | 43 | − |
| 10 | *Bacteridium sp.* CBS495-74 | 72 | 71 | − |
| 11 | *Bacillus cereus* IFO3131 | 80 | 28 | + |
| 12 | *Paracoccus denitrificans* IFO13301 | 68 | 41 | + |
| 13 | *Flavobacterium lutescens* IFO3084 | 52 | 59 | + |
| 14 | *Brevibacterium sp.* CBS717-73 | 62 | 52 | − |
| 15 | *Proteus mirabilis* IFO3849 | 42 | 18 | − |
| 16 | *Micrococcus sp.* CBS497-74 | 66 | 67 | − |
| 17 | *Rhodococcus erythropolis* IFO12320 | 66 | 56 | + |
| 18 | *Candida rugosa* ATCC14830 | 56 | 20 | − |
| 19 | *Rhodotorula minuta* var. *texensis* IFO879 | 39 | 32 | − |

*Optical purity of unreacted starting material after the completion of reaction.

EXAMPLES 20 & 21

The procedure of Example 1 was substantially repeated, provided however that the starting materials and microorganisms set forth in Table 2 were used. The results are summarized in Table 2. It is noted that the identification of the products and the measurement of their optical purity and rotatory polarization were carried out in similar manners as applied in Example 1.

TABLE 2

| Example | Microorganisms used | Starting material | Products | Rate of hydrolysis (%) | Optical purity*1 (% ee) | Rotatory polarization |
|---|---|---|---|---|---|---|
| 20 | *Corynebacterium flavescens* IAM 1642 | $\text{CH}_2\text{—CH—COOC}_2\text{H}_5$ with OH and Cl | $\text{CH}_2\text{—CH—COOH}$ with OH and Cl | 59 | 100 | nd*2 |
| 21 | *Pseudomonas aeruginosa* ATCC 15522 | $\text{C}_2\text{H}_5\text{OCO—CH—CH—COOC}_2\text{H}_5$ with OH and Cl (Erythro-Form) | $\text{HOOC—CH—CH—COOC}_2\text{H}_5$ with OH and Cl | 49 | 37*3 | + |

*1Optical purity of unreacted starting material after the completion of reaction
*2Undetermined
*3For optical splitting, Eu(tfmc)³ was added as a shift reagent (LSR) and determination was carried out by ¹H-NMR.

EXAMPLES 22 to 35

The procedure of Example 1 was substantially repeated, except that the microorganisms set forth in Table 3 were used in place of *Corynebacterium flavescens* IAM 1642. The results are shown in Table 3.

TABLE 3

| Example | Microorganisms used | Rate of hydrolysis (%) | Optical purity* (% ee) | Rotatory polarization |
|---|---|---|---|---|
| 22 | Achromobacter lyticus IFO12725 | 64 | 29 | + |
| 23 | Corynebacterium hydrocarbooxydans ATCC21767 | 77 | 35 | − |
| 24 | Pseudomonas aeruginosa ATCC15522 | 38 | 18 | − |
| 25 | Pseudomonas aeruginosa ATCC15523 | 34 | 19 | − |
| 26 | Pseudomonas diminuta IFO13181 | 87 | 36 | + |
| 27 | Pseudomonas diminuta IFO13182 | 81 | 30 | + |
| 28 | Pseudomonas pseudoalcaligenes ATCC12815 | 46 | 19 | − |
| 29 | Bacteridium sp. CBS946-74 | 57 | 32 | − |
| 30 | Bacillus subtilis IFO3108 | 59 | 52 | + |
| 31 | Bacillus sp. CBS494-74 | 49 | 46 | − |
| 32 | Brevibacterium imperiale CBS498-74 | 82 | 90 | − |
| 33 | Brevibacterium paraffinoliticum ATCC21195 | 34 | 21 | − |
| 34 | Micrococcus paraffinolyticus ATCC15582 | 64 | 44 | − |
| 35 | Rhodococcus equi IFO3730 | 34 | 20 | − |

*Optical purity of unreacted starting material after the completion of reaction.

EXAMPLE 36

Corynebackerium flavescens IAM 1642 was inoculated on 25 l of a bouillon medium (Nissui Seiyaku Co., Ltd.) and cultured at 30° C. for 45 hrs. After culturing, the microbial cells were collected and washed, and were then suspended at $OD_{660} = 5$ in a 1/15M 2-(N-Morpholine) ethanesulfornic acid buffer of pH 6, which is called MES buffer purchased from DOJINDO Laboratories, containing 25 g/l of ethyl erythro-2-chloro-3-hydroxybutyrate and a reaction was performed for 118 hrs.

It is noted that the identification of the products and the measurement of their optical purity and rotatory polarization were carried out in similar manners as applied in Example 1. In consequence, the rate of hydrolysis was found to be 75%, and it was found that (+)-ethyl erythro-2-chloro-3-hydroxy butyrate with an optical purity of 98% ee and (−)-erythro-2-chloro-3-hydroxybutyric acid with an optical purity of 46% ee were obtained in yields of 32.47 g and 87.20 g, respectively.

EXAMPLES 37 to 50

The procedure of Example 1 was substantially repeated, provided however that ethyl 2-chloro-3-hydroxypropionate was used for the starting material and microorganisms set forth in Table 4 were used and that the reaction was formed at $OD_{660} = 10$. The results are shown in Table 4.

TABLE 4

| Example | Microorganisms used | Rate of hydrolysis (%) | Optical purity* (% ee) | Rotatory polarization |
|---|---|---|---|---|
| 37 | Chromobacterium chocolatum IFO3758 | 64 | 98 | + |
| 38 | Corynebacterium flavescens IAM1642 | 59 | 100 | + |
| 39 | Corynebacterium hydrocarbooxydans ATCC21767 | 73 | 21 | + |
| 40 | Pseudomonas aeruginosa ATCC15522 | 34 | 17 | − |
| 41 | Pseudomonas diminuta IFO13181 | 69 | 31 | − |
| 41 | Pseudomonas diminuta IFO13182 | 74 | 36 | − |
| 43 | Bacteridium sp. CBS495-74 | 71 | 16 | + |
| 44 | Bacteridium sp. CBS496-74 | 82 | 32 | + |
| 45 | Flavobacterium lutescens IFO3084 | 50 | 25 | + |
| 46 | Micrococcus paraffinolyticus ATCC15582 | 75 | 27 | + |
| 47 | Micrococcus sp. CBS497-74 | 77 | 28 | + |
| 48 | Nocardia sp. ATCC21145 | 57 | 24 | − |
| 49 | Rhodococcus erythropolis IFO12320 | 74 | 13 | − |

TABLE 4-continued

| Example | Microorganisms used | Rate of hydrolysis (%) | Optical purity* (% ee) | Rotatory polarization |
|---|---|---|---|---|
| 50 | Rhodococcus equi IFO3730 | 74 | 21 | + |

*Optical purity of unreacted starting material after the completion of reaction.

EXAMPLE 51

*Chromobacterium chocolatum* IFO 3758 was inoculated on medium which contains 20 g of soluble starch (Extra pure reagent, Wako Pure Chemical Industries, Ltd., Osaka), 10 g of Bact Yeast extract (Difco Laboratories, Detroit, Mich., USA), 10 g of Polypepton (Nippon Seiyaku Co., Ltd.) and 2 liters of distilled water, and cultured for 48 hours. After culturing, the microbial cells were collected and washed, and were then suspended at $OD_{660}$ = 30 in a 1/15M MES buffer (DOJINDO Laboratories) of pH 6 containing 50 g/l of ethyl 2-chloro-3-hydroxypropionate and a reaction was performed at 30° C. for 8 hours. In consequence, the rate of hydrolysis was found to be 77%, and it was found that (+) ethyl 2-chloro-3-hydroxypropionate with an optical purity of 98% ee and (−) 2-chloro-3-hydroxypropionic acid were obtained in yields of 1.9 g and 4.1 g, respectively.

What is claimed is:

1. A method for preparing at least one optically active substance of the following formulae:

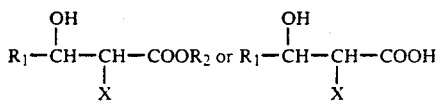

wherein $R_1$ is selected from the group consisting of a hydrogen atom, an alkyl group, a substituted phenyl group and an unsubstituted phenyl group, $R_2$ is an alkyl group and X is a halogen atom, which comprises asymmetrically hydrolyzing an ester of the following formula:

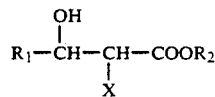

wherein $R_1$ is selected from the group consisting of a hydrogen atom, an alkyl group, a substituted phenyl group and an unsubstituted phenyl group, wherein the ester is of the erythro type in the case that $R_1$ is selected from the group consisting of an alkyl group, a substituted phenyl group and an unsubstituted phenyl group, $R_2$ is an alkyl group and X is a halogen atom, with a microorganism capable of asymmetrically hydrolyzing said ester, said microorganism selected from the group consisting of *Achromobacter lyticus* IFO 12725, *Achromobacter lyticus* IFO 12726, *Acinetobacter calcoaceticus* IFO 12552, Arthrobacter sp. ATCC 27778, *Erwinia herbicola* ATCC 21434, *Klebsiella pneumoniae* IFO 3318, *Chromobacterium chocolatum* IFO 3758, *Corynebacterium flavescens* IAM 1642, *Corynebacterium hydrocarbooxydans* ATCC 21767, *Pseudomonas aeruginosa* ATCC 15522, *Pseudomonas aeruginosa* ATCC 15523, *Pseudomonas diminuta* IFO 13181, *Pseudomonas pseudoalcaligenes* ATCC 12815, *Pseudomonas oleovorans* ATCC 29347, *Paracoccus denitrificans* IFO 13301, *Brevibacterium paraffinoliticum* ATCC 21195, *Micrococcus paraffinolyticus* ATCC 15582, *Rhodococcus erythropolis* IFO 12320, *Candida rugosa* ATCC 14830, Norcardia sp. ATCC 21145, *Flavobacterium lutescens* IFO 3084 and combinations thereof.

2. The method as claimed in claim 1, wherein said asymmetrically hydrolyzing is performed under a condition of a concentration of the ester from 1 to 500 grams per liter at a temperature of from 0° to 60° C. at a pH of from 4 to 11.

3. A method for preparing an optically active substance of the following formulae:

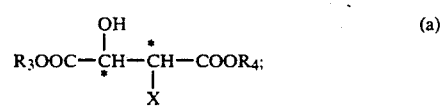

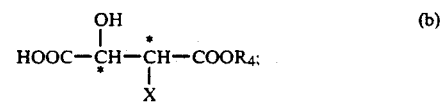

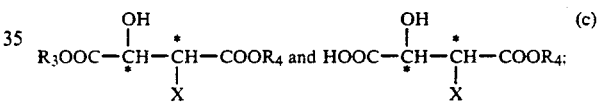

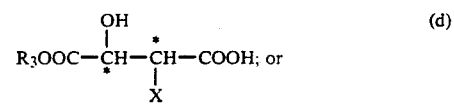

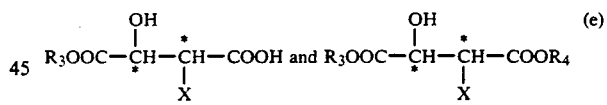

wherein $R_3$ and $R_4$, which may be identical with or different from each other, is an alkyl group and X is a halogen atom, which comprises asymmetrically hydrolyzing an ester expressed by the following formula:

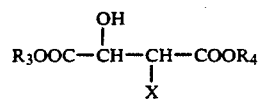

wherein $R_3$, $R_4$ and X have the same meanings as defined above, with a microorganism capable of asymmetrically hydrolyzing said ester, said microorganism selected from the group consisting of *Achromobacter lyticus* IFO 12725, *Achromobacter lyticus* IFO 12726, *Acinetobacter calcoaceticus* IFO 12552, Arthrobacter sp. ATCC 27778, *Erwinia herbicola* ATCC 21434, *Klebsiella pneumoniae* IFO 3318, *Chromobacterium chocolatum* IFO 3758, *Corynebacterium flavescens* IAM 1642, *Corynebacterium hydrocarbooxydans* ATCC 21767, Pseudomonas aeruginosa ATCC 15522, Pseudomonas aeruginosa ATCC 15523, Pseudomonas diminuta IFO 13181, Pseudomonas pseudoalcaligenes ATCC 12815, Pseudomonas oleovorans ATCC 29347, Paracoccus denitrificans IFO 13301, Brevibacterium paraffinoliticum ATCC 21195, Micrococcus paraffinolyticus ATCC 15582, Rhodococcus erythropolis IFO 12320, Candida rugosa ATCC 14830, Norcardia sp. ATCC 21145, Flavobacterium lutescens IFO 3084 and combinations thereof.

4. The method as claimed in claim 3, wherein said asymmetrically hydrolyzing is performed under a condition of a concentration of the ester from 1 to 500 grams per liter at a temperature of from 0° to 60° C. at a pH of from 4 to 11.

5. The method as claimed in claim 1, wherein X is selected from the group consisting of Cl, Br and I.

6. The method as claimed in claim 1, wherein for $R_1$ the substituted phenyl group is substituted by a halogen atom, a hydroxyl group, a methoxy group or an alkyl group.

7. The method as claimed in claim 1, wherein said asymmetrically hydrolyzing is performed with a concentration of the ester of 5 to 100 grams per liter at a temperature of 10° to 40° C. and at a pH of from 6 to 8.

8. The method as claimed in claim 1, wherein the ester is ethyl erythro-2-chloro-3-hydroxybutyrate.

9. The method as claimed in claim 1, wherein the optically active substance is (+) ethyl-erythro-2-chloro-3-hydroxybutyrate.

10. The method as claimed in claim 1, wherein the optically active substance is (−) -erythro-2-chloro-3-hydroxybutyric acid.

11. The method as claimed in claim 1, wherein the ester is ethyl 2-chloro-3-hydroxypropionate.

12. The method as claimed in claim 1, wherein the optically active substance is (+) ethyl 2-chloro-3-hydroxypropionate.

13. The method as claimed in claim 1, wherein the optically active substance is (−) 2-chloro-3-hydroxypropionic acid.

14. The method as claimed in claim 3, wherein the ester is

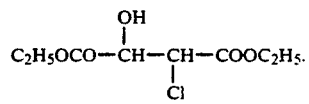

15. The method as claimed in claim 3, wherein the optically active substance is

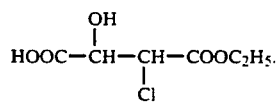

16. The method as claimed in claim 3, wherein said asymmetrical hydrolyzing is performed with a concentration of the ester of 5 to 100 grams per liter at a temperature of 10° to 40° C. and at a pH of from 6 to 8.

17. The method as claimed in claim 1, wherein the optically active substance is of the erythro type.

18. The method as claimed in claim 3, wherein the optically active substance is of the erythro type.

* * * * *